(12) United States Patent
Ricke (10) Patent No.: US 7,907,992 B2
(45) Date of Patent: Mar. 15, 2011

(54) METHOD AND SYSTEM FOR PACEMAKER PULSE DETECTION

(75) Inventor: Anthony David Ricke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 842 days.

(21) Appl. No.: 11/835,653

(22) Filed: Aug. 8, 2007

(65) Prior Publication Data

US 2009/0043354 A1 Feb. 12, 2009

(51) Int. Cl.
*A61B 5/04* (2006.01)
(52) U.S. Cl. .................................... 600/510
(58) Field of Classification Search ............. 600/523; 607/27
See application file for complete search history.

(56) References Cited

U.S. PATENT DOCUMENTS

| | | | | |
|---|---|---|---|---|
| 5,682,902 A | * | 11/1997 | Herleikson | 600/521 |
| 5,771,898 A | * | 6/1998 | Marinello | 600/510 |
| 7,383,079 B2 | * | 6/2008 | Holland | 600/509 |

* cited by examiner

*Primary Examiner* — Mark W Bockelman
*Assistant Examiner* — Elizabeth K So
(74) *Attorney, Agent, or Firm* — Andrus, Sceales, Starke & Sawall, LLP (57) ABSTRACT

A cardiac monitoring system is disclosed herein. The cardiac monitoring system includes a sensor adapted to collect an ECG signal that comprises a pacemaker signal and a cardiac signal. The cardiac monitoring system also includes a data acquisition module adapted to receive the ECG signal from the sensor. The data acquisition module includes a signal path adapted to isolate the pacemaker signal from the remainder of the ECG signal, and a processor adapted to identify a pace pulse on the isolated pacemaker signal.

13 Claims, 6 Drawing Sheets

METHOD AND SYSTEM FOR PACEMAKER PULSE DETECTION

BACKGROUND OF THE INVENTION

The present invention relates generally to the field of implanted medical devices. More precisely, the invention relates to the detection of pacing stimulus artifacts such as electrocardiogram (ECG) signal pulses that are derived from implanted electronic pacemakers.

Detection of pacing stimulus artifacts from implanted electronic pacemakers is sometimes difficult due to sophisticated and more evolved generations of implanted devices that stimulate the heart muscle. In addition, artifacts in the body surface ECG have gotten smaller and/or more complicated in shape and sequence. Further, the transmission of the pacing stimulus artifacts through biological tissue and the alignment of the ECG sensors with the pacing stimulus transmission vector can modify artifact morphology thereby rendering them more difficult to identify.

BRIEF DESCRIPTION OF THE INVENTION

The above-mentioned shortcomings, disadvantages and problems are addressed herein which will be understood by reading and understanding the following specification.

In an embodiment, a cardiac monitoring system includes a sensor adapted to collect an ECG signal that comprises a pacemaker signal and a cardiac signal. The cardiac monitoring system also includes a data acquisition module adapted to receive the ECG signal from the sensor. The data acquisition module includes a signal path adapted to isolate the pacemaker signal from the remainder of the ECG signal, and a processor adapted to identify a pace pulse on the isolated pacemaker signal.

In another embodiment, a method for identifying a pace pulse on an ECG signal includes providing an ECG signal, and isolating a pacemaker signal from the remainder of the ECG signal. Isolating the pacemaker signal includes filtering the ECG signal, and sampling the ECG signal at a predefined sampling rate. The method for identifying a pace pulse on an electrocardiograph signal also includes identifying a pulse defined by the isolated pacemaker signal, measuring the identified pulse, and determining whether the identified pulse is a pace pulse.

In another embodiment, a method for identifying a pace pulse on an ECG signal includes identifying a pulse defined by an ECG signal, measuring the identified pulse to obtain pulse measurement data, conducting a morphological analysis of the identified pulse based on the pulse measurement data, and determining whether the identified pulse is a pace pulse based on the morphological analysis.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
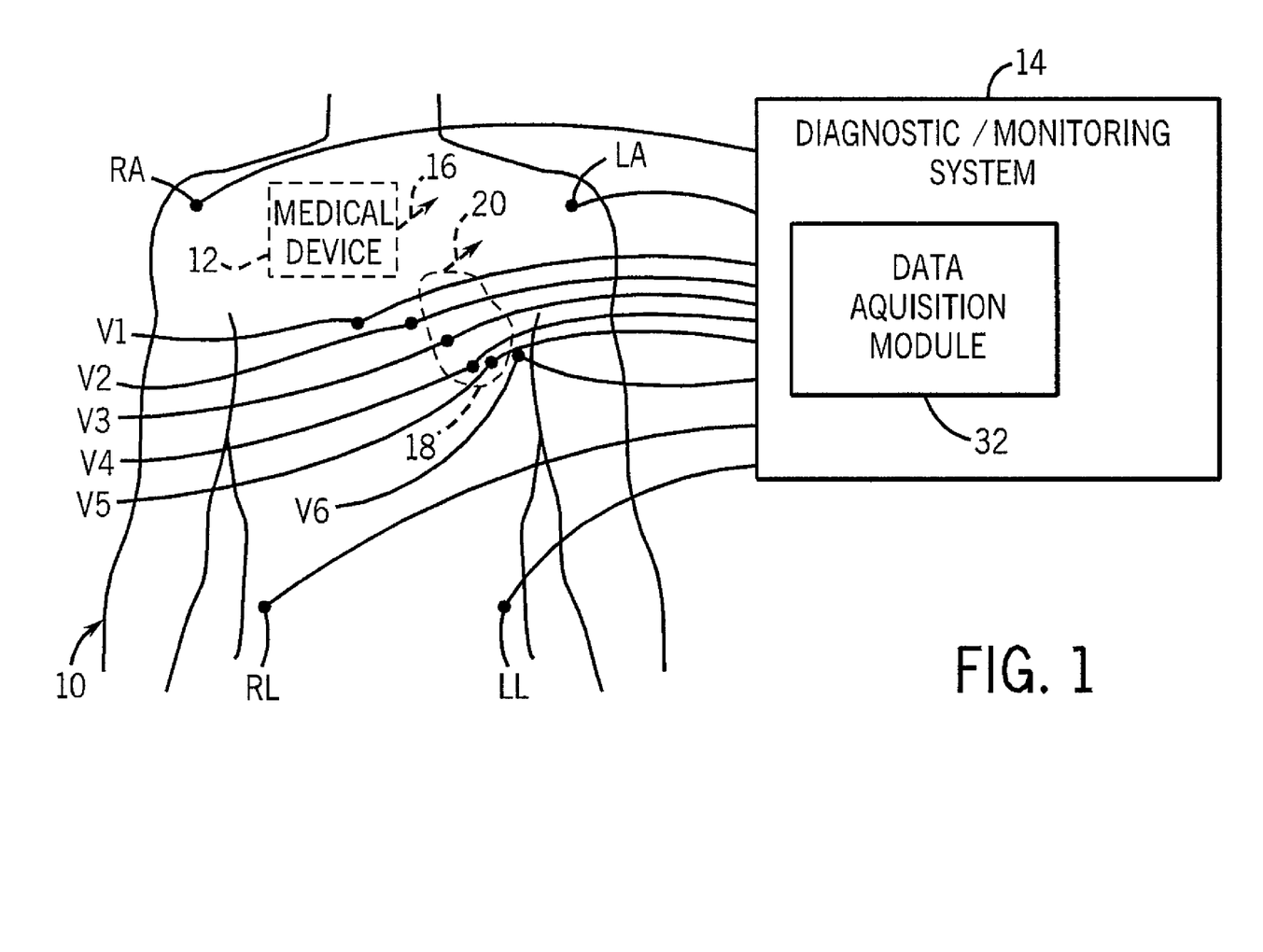
FIG. 1 is a schematic diagram illustrating a cardiac diagnostic/monitoring system operatively connected to a patient having an implanted medical device.

Referring to FIG. 1, a patient 10 having an implanted medical device 12 is operatively connected to a cardiac diagnostic/monitoring system 14 in accordance with an embodiment. The implanted medical device 12 will hereinafter be referred to as an artificial pacemaker 12, and the cardiac diagnostic/monitoring system 14 will hereinafter be referred to as an electrocardiograph 14.

The pacemaker 12 generates an electrical output 16 which may include a pacing stimulus adapted to regulate to the patient's heart 18. According to one embodiment, the output 16 defines a plurality of artifacts such as, for example, the generally trapezoidal pulses 92 (shown in FIG. 5).

Figure 2:
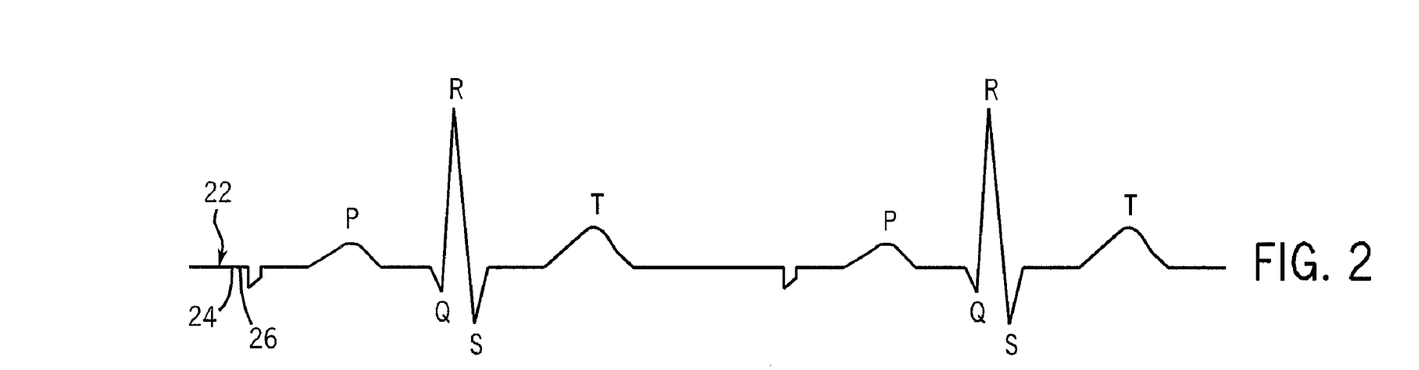
FIG. 2 is an illustrative ECG signal.

The electrocardiograph 14 is adapted to measure an electrical output 20 generated by the patient's heart 18, and the output 16 generated by the pacemaker 12. Referring to FIGS. 1-2, the measured outputs 16, 20 are initially recorded by the electrocardiograph 14 in the form of an ECG signal 22. The ECG signal 22 generally comprises a pacemaker signal 24 that is reflective of the output 16, and a cardiac signal 26 that is reflective of the output 20. Therefore, for purposes of this disclosure, the pacemaker signal 24 may be defined as the signal measured by the electrocardiograph 14 in response to the pacemaker output 16, and the cardiac signal 26 may be defined as the signal measured by the electrocardiograph 14 in response to the cardiac electrical activity 20.

Figure 2A:
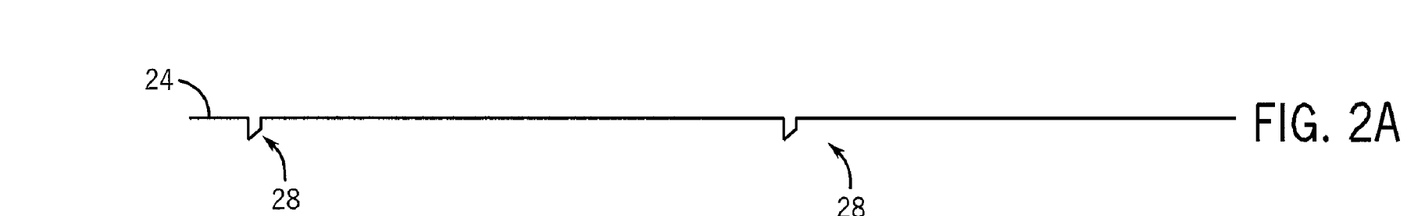
FIG. 2a is an illustrative pacemaker signal isolated from the remainder of the ECG signal of FIG. 2.
Figure 2B:
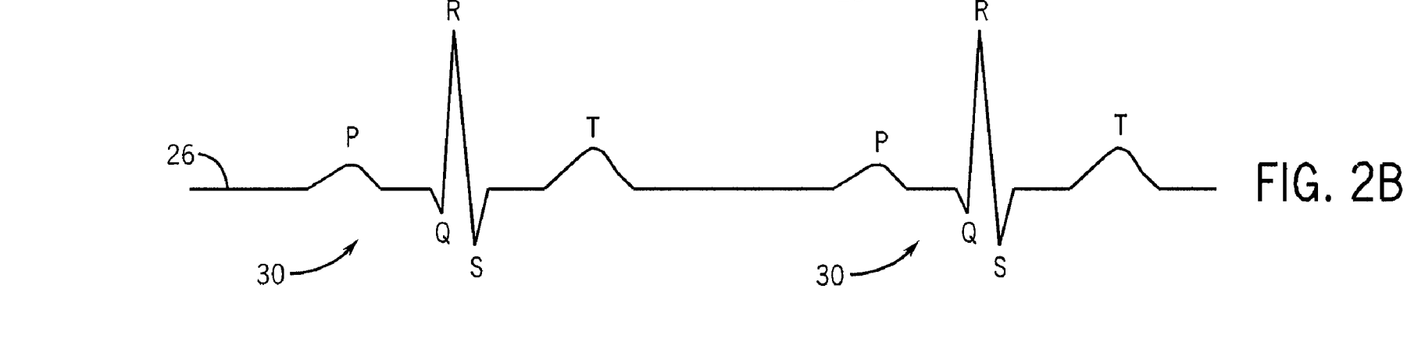
FIG. 2b is an illustrative cardiac signal isolated from the remainder of the ECG signal of FIG. 2.

As shown in FIG. 2a, an illustrative pacemaker signal 24 has been isolated from the remainder of the ECG signal 22 of FIG. 2. The illustrative pacemaker signal 24 includes a plurality of pace pulses 28. For purposes of this disclosure, a "pace pulse" is defined to include an ECG signal pulse generated in response to pacemaker output 16 (shown in FIG. 1). As shown in FIG. 2b, an illustrative cardiac signal 26 has been isolated from the remainder of the ECG signal 22 of FIG. 2. The illustrative cardiac signal 26 includes a plurality of PQRST complexes 30 reflective of typical cardiac electrical activity. It should be appreciated that the cardiac signal 26 may not be completely isolated (i.e., the filtration process may not remove all extraneous data) such that the isolated cardiac signal 26 still contains some pacemaker data.

Referring again to FIG. 1, the electrocardiograph 14 can be coupled to the patient 10 by an array of sensors or transducers. In the illustrated embodiment, the array of sensors include a right arm electrode RA; a left arm electrode LA; chest electrodes V1, V2, V3, V4, V5 and V6; a right leg electrode RL; and a left leg electrode LL for acquiring a standard twelve lead, ten-electrode electrocardiogram (ECG) signal. It should be appreciated that the electrode configuration of FIG. 1 is provided for illustrative purposes, and that other electrode configurations can be envisioned.

Figure 3:
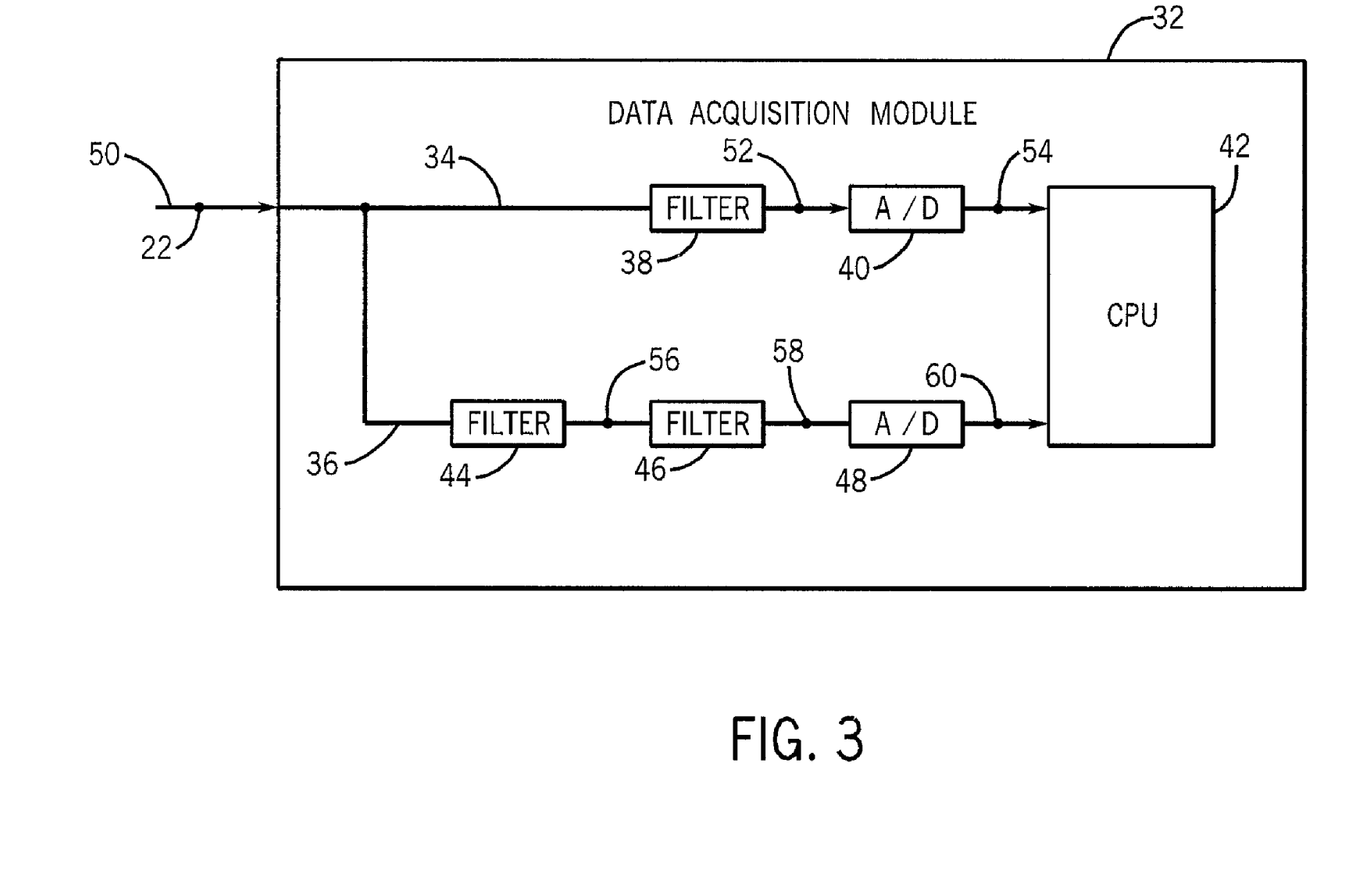
FIG. 3 is a schematic diagram illustrating a data acquisition module in accordance with an embodiment.

The electrocardiograph 14 includes a data acquisition module 32. Referring to FIG. 3, the data acquisition module 32 is shown in more detail. According to one embodiment, the data acquisition module 32 defines a first signal path 34 and a second signal path 36. The first signal path 34 is directed through a low-pass filter 38, an analog to digital (A/D) converter 40, and to a central processing unit (CPU) 42. The second signal path 36 is directed through a low-pass filter 44, a high-pass filter 46, an A/D converter 48, and to the CPU 42.

The first signal path 34 is adapted to isolate the cardiac signal 26 (shown in FIG. 2b), and the second signal path 36 is adapted to isolate the pacemaker signal 24 (shown in FIG. 2a). Using two distinct signal paths 34, 36 to isolate the cardiac signal 26 and the pacemaker signal 24 allows for pacemaker pulse detection in a manner that minimizes the introduction of noise into the cardiac signal 26. The bandwidth of the cardiac signal 26 is between approximately 0.5 and 500 Hz, whereas the bandwidth of the pacemaker signal 24 is between approximately 250 Hz and 10 kHz. There is very little man-made noise that can corrupt the cardiac signal 26 because of its narrow bandwidth and low frequency. Opening up the bandwidth of the cardiac signal 26 by an amount necessary to detect pacemaker pulses could introduce the system to more noise thereby rendering subsequent cardiac signal analysis more difficult.

The use of two distinct signal paths 34, 36 to isolate the cardiac signal 26 and the pacemaker signal 24 also advantageously allows for the implementation of less expensive components thereby reducing the overall cost of the system. As is known in the art, the cardiac signal 26 generally requires direct current (DC) coupling whereas the pacemaker signal 24 can implement alternating current (AC) coupling. AC couplings implement 12 bit A/D converters that cost less than the 16 bit A/D converters required for DC couplings.

The data acquisition module 32 includes an input 50 adapted to receive a signal such as the analog ECG signal 22 from one or more of the sensors RA, LA, V1, V2, V3, V4, V5, V6, RL, and LL (shown in FIG. 1). It should be appreciated that the schematically depicted input 50 and ECG signal 22 may respectively represent one or more inputs and one or more signals. According to one embodiment, the input 50 represents the inputs I, II, III, aVR, aVL, aVF, V1, V2, V3, V4, V5, and V6 (not shown) which may be derived from the sensors RA, LA, V1, V2, V3, V4, V5, V6, RL, and LL in a known manner.

Having described the apparatus of the data acquisition module 32 in accordance with an embodiment, its operation will hereinafter be described. The operation of the data acquisition module 32 will begin with a description of the signal path 34, and thereafter the signal path 36 will be described.

The signal path 32 is configured to operate in the following manner. The ECG signal 22 is transmitted along the signal path 32 through the low-pass filter 38 in order to remove unwanted noise. As is known in the art, a low-pass filter is a filter that passes low frequency signals well, and that attenuates or reduces frequencies above a cutoff frequency. According to one embodiment, the low-pass filter 38 is an anti-aliasing filter having a cutoff frequency of approximately 500 hertz (Hz). The low-pass filter 38 removes high frequency content from the ECG signal 22 to produce the ECG signal 52. The filtration of a signal to remove unwanted noise is well known in the art and therefore will not be described in detail.

Still following the signal path 34, the ECG signal 52 is transmitted from the low-pass filter 38 to the A/D converter 40. The A/D converter 40 is adapted to convert the analog ECG signal 52 into a digital ECG signal 54 at a predefined sampling rate. According to one embodiment, the A/D converter 40 sampling rate is approximately 2 kilohertz/second (kHz/Sec). The digital ECG signal 54 is transmitted to the CPU 42. The digital ECG signal 54 comprises a cardiac signal such as the cardiac signal 26 (shown in FIG. 2b). It has been observed that the filtration and sampling of the ECG signal 54 in the manner described renders a clear depiction of the constituent cardiac signal data and is therefore particularly well suited for the analysis of a patient's cardiac activity.

The signal path 36 is configured to operate in the following manner. The ECG signal 22 is transmitted along the signal path 36 through the low-pass filter 44 in order to remove unwanted noise. According to one embodiment, the low-pass filter 44 is an anti-aliasing filter having a cutoff frequency of approximately 15 kHz. The low-pass filter 44 removes high frequency content from the ECG signal 22 to produce the ECG signal 56.

The ECG signal 56 is transmitted from the low-pass filter 44 to the high-pass filter 46 in order to remove cardiac data and thereby isolate the portion of the ECG signal 56 containing pacemaker data. As is known in the art, a high-pass filter is a filter that passes high frequency signals well, and that attenuates or reduces frequencies below a cutoff frequency. According to one embodiment, the cutoff frequency of the high-pass filter 46 is approximately 5 Hz. The high-pass filter 46 is configured to convert the ECG signal 56 into the ECG signal 58.

Still following the signal path 36, the ECG signal 58 is transmitted from the high-pass filter 46 to the A/D converter 48. The A/D converter 48 is adapted to convert the analog ECG signal 58 into a digital ECG signal 60 at a predefined sampling rate. According to one embodiment, the A/D converter 48 sampling rate is approximately 75 kHz/Sec. The digital ECG signal 60 is transmitted to the CPU 42. The digital ECG signal 60 comprises an isolated pacemaker signal such as the pacemaker signal 24 (shown in FIG. 2a). It has been observed that the filtration and sampling of the ECG signal 60 in the manner described renders a clear depiction of the constituent pacemaker signal and is therefore particularly well suited for the analysis of pacemaker functionality.

Figure 4:
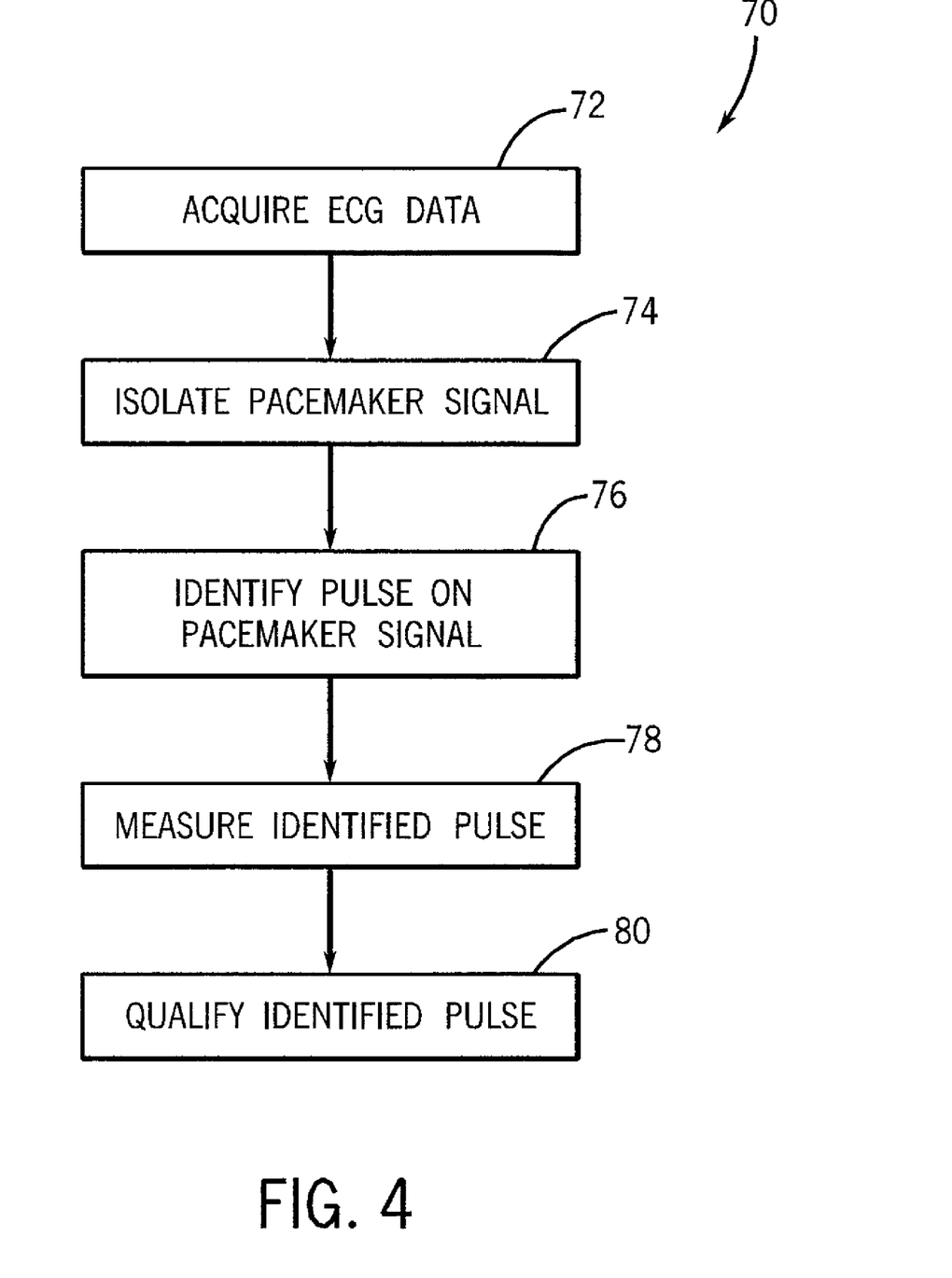
FIG. 4 is a flow chart illustrating a method in accordance with an embodiment.

Referring to FIG. 4, a flow chart illustrating a method 70 for pacemaker pulse detection is shown. The individual blocks 72-80 of the flow chart represent steps that may be performed in accordance with the method 70. Steps 76-80 in particular may be performed by the CPU 42 (shown in FIG. 3).

At step 72, ECG data is collected. The collection of ECG data may, for example, comprise obtaining an ECG signal such as the ECG signal 22 (shown in FIG. 2) with an electrocardiograph device such as the electrocardiograph 14 (shown in FIG. 1). At step 74, a pacemaker signal such as the pacemaker signal 24 (shown in FIG. 2a) is isolated. The term "isolating a signal" as used herein may be defined to include the removal of one or more unwanted signals or signal frequencies such as through filtration, and/or the process of collecting specific portions of a signal such as through sampling. The isolation of a pacemaker signal at step 74 may be performed in the manner previously described with respect to the low-pass filter 44, the high-pass filter 46, and the A/D converter 48 (shown in FIG. 3).

At step 76, any pulses in the isolated pacemaker signal obtained at step 74 are identified. The pulses identified at step 76 include any signal pulses and are not limited to pace pulses. According to one embodiment, pulses may be identified by an analysis of the significant slopes defined by a signal. A "significant slope" may be defined as a signal slope having an absolute value that exceeds a predefined limit such as, for example, 0.3 milivolts/100 microseconds. The number of significant slopes, the duration between significant slopes, the sequence of significant slope signs (i.e., either positive or negative), and the magnitude of the significant slopes may be implemented to identify pulses. A finite state machine (not shown) may also be implemented in a known manner to assist in the identification of pulses. The identification of pulses in a signal is well known to those skilled in the art and therefore will not be described in further detail.

At step 78, any pulses identified at step 76 are measured. The measurement of an identified pulse at step 78 may include the measurement of any characteristic or feature of the pulse, and may further include the measurement of portions of a signal preceding and/or superseding the pulse.

At step 80, any pulses identified at step 76 are qualified based on the measurement data obtained at step 78. The qualification of a pulse at step 80 refers to the determination of whether a given pulse is a pace pulse. Therefore, an identified pulse is either qualified at step 80 as a pace pulse or a non-pace pulse. In a non-limiting manner, pulse qualification at step 80 may be based on pulse height, the differential between leading edge height and trailing edge height, pulse duration, and/or the slope of various portions of the pulse.

According to one embodiment, pulse qualification at step 80 may be based on the slope of a pacemaker signal segment defined just prior to (e.g., 1 millisecond before) the leading edge of the pulse. According to another embodiment, pulse qualification at step 80 may be based on the number of significant slopes of a pacemaker signal segment defined just prior to (e.g., 1 millisecond before), during, and just after (e.g., 1 millisecond after) the pulse. According to yet another embodiment, pulse qualification at step 80 may be based on a morphology analysis of the pulse. As is known in the art, a morphology analysis of a pulse refers to the analysis of pulse shape. Therefore, the measurement data of step 78 may be implemented to identify a given pulse shape, and if the identified pulse shape is consistent with one of a recognized category of pacemaker pulse shapes (e.g., one of the shapes 120-140 depicted in FIGS. 5-9), the identified pulse may be qualified as pace pulse.

Figure 5:
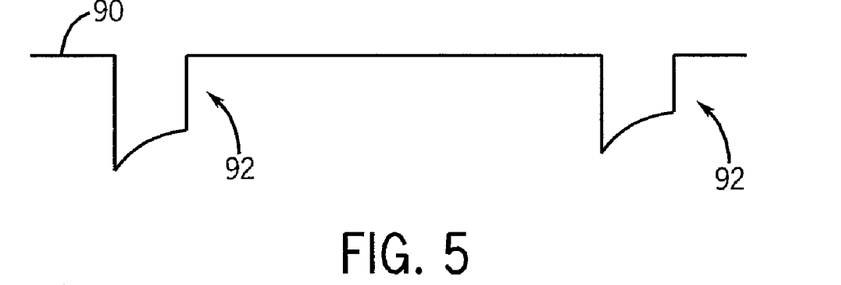
FIG. 5 is a schematic representation of a pacemaker output signal in accordance with an embodiment.

Referring to FIG. 5, the pacemaker output 16 (shown in FIG. 1) is schematically represented by an output signal 90. According to one embodiment, the output signal 90 comprises a plurality of trapezoidal pulses 92 that are detectable and recordable by the electrocardiograph 14 (shown in FIG. 1). It should be appreciated that, in some instances, the electrocardiograph 14 may record a modified version of the pulses 92 (e.g., the pace pulses 100b-100d shown in FIGS. 5-9). There are a number of reasons why the shape or morphology of the recorded pace pulses 100b-100d can deviate from the pulses 92 such as, for example, the effects of signal transmission through biological tissue and/or the alignment of an electrocardiograph sensor with the pacemaker output signal vector. Pace pulses such as the pace pulses 100b-100d can deviate from their conventional trapezoidal shape to the extent that they become difficult to recognize as originating from a pacemaker. Advantageously, the pulse measurement data from step 78 of the method 70 (shown in FIG. 4) may be implemented to identify a wide variety of pace pulse morphologies in order to increase the likelihood that modified pace pulses are properly identified.

Figure 6:
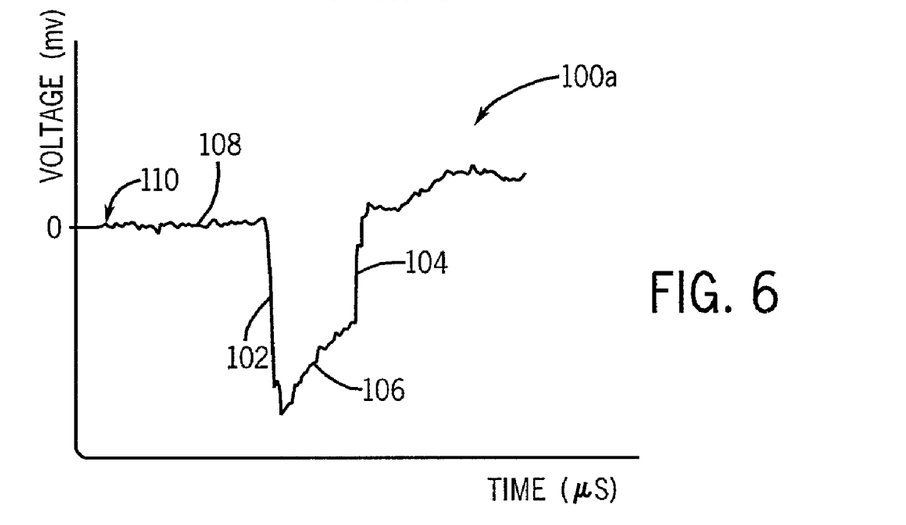
FIG. 6 is a schematic representation of an illustrative pace pulse morphology in accordance with an embodiment.

Referring to FIG. 6, a pace pulse 100a recorded by an electrocardiograph is shown in detail. The pace pulse 100a includes a leading edge 102, a trailing edge 104, and a pulse plateau 106. Pulses such as the pace pulse 100a that deviate only slightly from the trapezoidal pulses 92 are relatively easy to identify as pace pulses through a morphological analysis. The pace pulse 100a may be referred to as a uniphasic pulse because it extends away from the steady state zero voltage portion 108 of the signal 110 in a single direction only. A number of different pulse morphologies that are recognizable as being pace pulses will hereinafter be described with respect to FIGS. 7-9.

Figure 7:
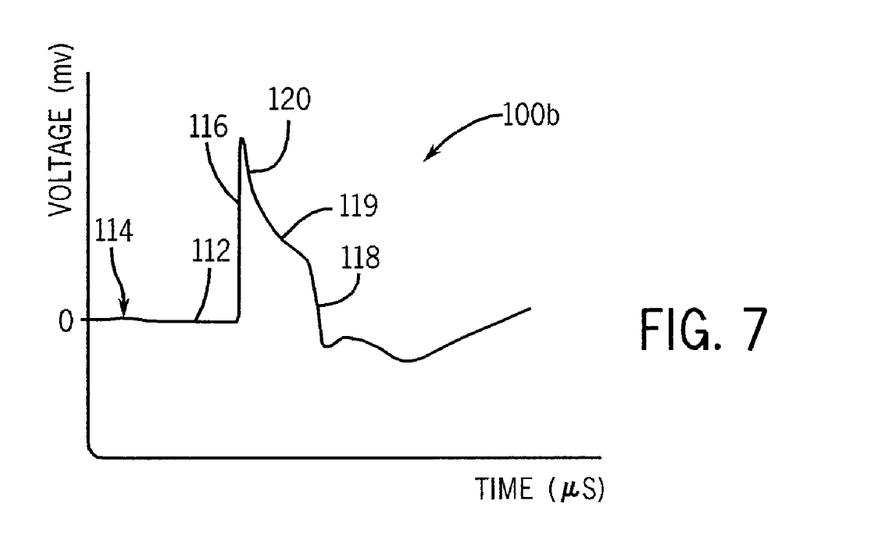
FIG. 7 is a schematic representation of an illustrative pace pulse morphology in accordance with an embodiment.

Referring to FIG. 7, a pace pulse 100b recorded by an electrocardiograph is shown in detail. The pace pulse 100b is also uniphasic because it extends away from the steady state zero voltage portion 112 of the signal 114 in a single direction only. The pace pulse 102b deviates more significantly from the trapezoidal pulses 92 in that the length of the leading edge 116 of the pulse 102b exceeds the length of the trailing edge 118 by a disproportionate amount. The morphology of the pulse 100b may therefore be identified by analyzing the lengths of the leading edge 116, the trailing edge 118, the pulse plateau 119 and/or the overshoot edge 120.

Figure 8:
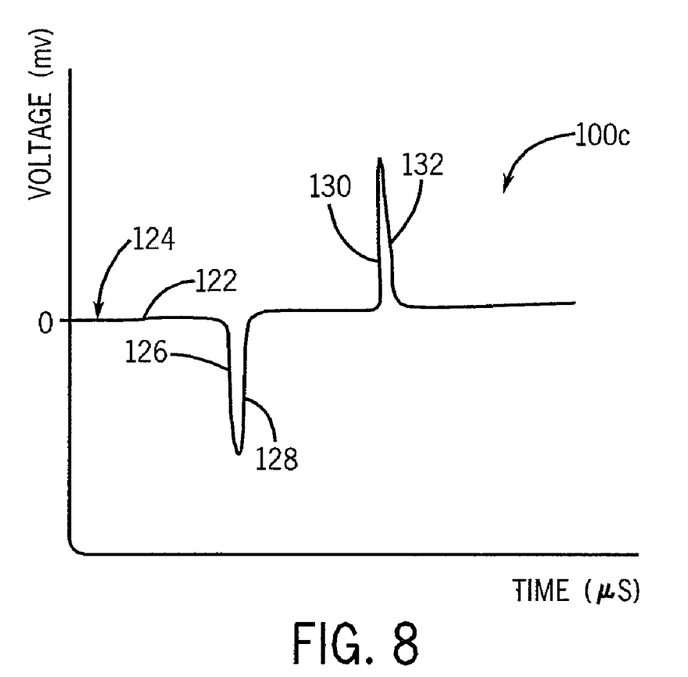
FIG. 8 is a schematic representation of an illustrative pace pulse morphology in accordance with an embodiment.

Referring to FIG. 8, a pace pulse 100c recorded by an electrocardiograph is shown in detail. The pace pulse 100c may be referred to as a biphasic pulse because it extends away from the steady state zero voltage portion 122 of the signal 124 in both (i.e., positive and negative) directions. Pulses such as the pace pulse 100c are difficult to properly identify as a single pacemaker pulse because they can appear to comprise two separate pulses with opposite polarities. The morphology of the pulse 100c may, for example, be identified by analyzing the significant slopes 126, 128, 130 and 132.

Figure 9:
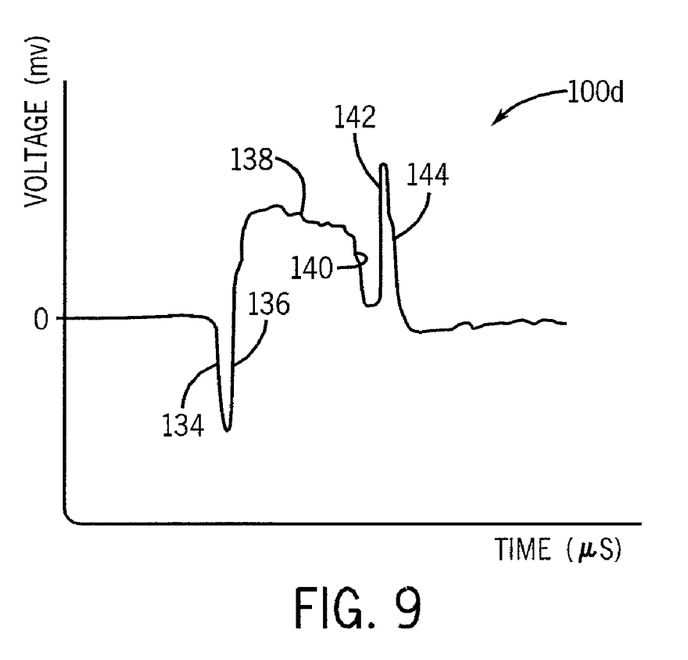
FIG. 9 is a schematic representation of an illustrative pace pulse morphology in accordance with an embodiment.

Referring to FIG. 9, a pace pulse 100d recorded by an electrocardiograph is shown in detail. The pace pulse 100d may be referred to as a polyphasic pulse. For purposes of this disclosure, a polyphasic pulse can be defined to include any pulse that cannot be classified as either uniphasic or biphasic. The morphology of the pulse 100c may, for example, be identified by analyzing the significant slopes 134, 136, 138, 140, 142 and 144.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

I claim:

1. A method for identifying a pace pulse on an ECG signal comprising a pacemaker signal and a cardiac signal, the method comprising:
    providing an ECG signal;
    isolating the pacemaker signal from the ECG signal by filtering the ECG signal to remove the cardiac signal from the ECG signal;
    sampling the isolated pacemaker signal at a predefined sampling rate;
    identifying a pulse defined by the isolated pacemaker signal;
    measuring a characteristics of the identified pulse; and
    determining whether the identified pulse is the pace pulse.

2. The method of claim 1, wherein said filtering the ECG signal further comprises passing the ECG signal through a low-pass filter to remove noise.

3. The method of claim 1, wherein said filtering the ECG signal comprises passing the ECG signal through a high-pass filter to remove the cardiac signal.

4. The method of claim 1, wherein said sampling the ECG signal comprises sampling the ECG signal at a rate of approximately 75 kilohertz/second.

5. The method of claim 1, wherein said identifying a pulse includes implementing a finite state machine to identify the pulse.

6. The method of claim 1, wherein said determining whether the identified pulse is the pace pulse includes analyzing the characteristic of the identified pulse.

7. The method of claim 1, wherein said determining whether the identified pulse is the pace pulse includes analyzing the morphology of the identified pulse.

8. The method of claim 1, wherein said determining whether the identified pulse is the pace pulse includes analyzing one or more significant slopes defined by the identified pulse.

9. A method of identifying a pace pulse in an electrocardiograph (ECG) signal comprising a pacemaker signal and a cardiac signal, the method comprising:
   receiving the ECG signal;
   isolating the pacemaker signal from the ECG signal and filtering the ECG signal to remove the cardiac signal from the ECG signal;
   sampling the isolated pacemaker signal at a first predetermined sampling rate;
   identifying a pulse in the isolated pacemaker signal;
   measuring a characteristic of the identified pulse;
   qualifying the identified pulse as the pace pulse based upon the measured characteristic; and
   analyzing a pacemaker functionality from the pace pulse.

10. The method of claim 9 further comprising:
    isolating the cardiac signal from the ECG signal by filtering the ECG signal to remove the pacemaker signal;
    sampling the isolated cardiac signal at a second predetermined sampling rate; and
    analyzing cardiac activity of a patient from the sampled isolated cardiac signal.

11. The method of claim 10, wherein the first predetermined sampling rate is greater than the second predetermined sampling rate.

12. The method of claim 11, wherein the first predetermined sampling rate is about 75 kilohertz/second.

13. The method of claim 11, wherein the second predetermined sampling rate is about 2 kilohertz/second.

* * * * *